United States Patent [19]

Massey et al.

[11] Patent Number: 5,746,974
[45] Date of Patent: May 5, 1998

[54] APPARATUS FOR IMPROVED LUMINESCENCE ASSAYS USING PARTICLE CONCENTRATION, ELECTROCHEMICAL GENERATION OF CHEMILUMINESCENCE AND CHEMILUMINESCENCE DETECTION

[75] Inventors: Richard J. Massey, Rockville; Gary F. Blackburn, Gaithersburg; Elizabeth W. Wilkins, Germantown; Jonathan K. Leland, Laurel, all of Md.

[73] Assignee: IGEN International, Inc., Gaithersburg, Md.

[21] Appl. No.: 467,028

[22] Filed: Jun. 6, 1995

Related U.S. Application Data

[62] Division of Ser. No. 348,749, Dec. 1, 1994, abandoned, which is a continuation of Ser. No. 728,093, Jul. 10, 1991, abandoned, which is a continuation-in-part of Ser. No. 652,427, Feb. 6, 1991, abandoned, which is a continuation-in-part of Ser. No. 539,389, Jun. 18, 1990, abandoned, which is a continuation of Ser. No. 266,882, Nov. 3, 1988, abandoned.

[51] Int. Cl.$^6$ ................................................. G01N 21/66
[52] U.S. Cl. ........................... 422/52; 422/82.05; 436/172
[58] Field of Search ............................ 422/82.05, 52; 436/172, 164

[56] References Cited

U.S. PATENT DOCUMENTS

| | | |
|---|---|---|
| 3,319,132 | 5/1967 | Chandross . |
| 3,970,518 | 7/1976 | Giaever . |
| 4,070,246 | 1/1978 | Kennedy et al. . |
| 4,115,535 | 9/1978 | Giaever . |
| 4,169,804 | 10/1979 | Yapel, Jr. . |
| 4,280,815 | 7/1981 | Oberhardt et al. . |
| 4,305,925 | 12/1981 | Kapmeyer et al. . |
| 4,419,453 | 12/1983 | Dorman et al. . |

(List continued on next page.)

FOREIGN PATENT DOCUMENTS

| | | |
|---|---|---|
| 0030 087 | 6/1981 | European Pat. Off. . |
| 0180384 | 5/1988 | European Pat. Off. . |
| 1500127 | 2/1978 | United Kingdom . |
| 2005019 | 3/1979 | United Kingdom . |
| 2074727 | 11/1981 | United Kingdom . |

(List continued on next page.)

OTHER PUBLICATIONS

Abruna, J. Electrochem. Soc. 1985, 132, 842.
Beaucage SL, Caruthers MH. Deoxynucleoside phosphoramidites, a new class of key intermediates for deoxypolynucleotide synthesis. *Tetrahedron Lett* 1982; 22:1859–62.
Cardullo RA, Agrawal S, Flores C, Zamecnik DC, Wolf DE. Detection of nucleic acid hybridization by nonradiative fluorescene resonance energy transfer. *Proc. Natl. Acad. Sci.* 1988; 85:8790–4.

(List continued on next page.)

*Primary Examiner*—Lyle A. Alexander
*Attorney, Agent, or Firm*—Curtis, Morris & Safford, P.C.; Barry Evans, Esq.; David Rubin, Esq.

[57] ABSTRACT

What is described are methods and apparatus for performing a binding assay for an analyte of interest present in a sample. The methods include the steps of: forming a composition containing said sample, an assay-performance-substance which contains a component linked to a label compound capable of chemiluminescing when triggered, and a plurality of coated magnetic particles capable of specifically binding with the analyte and/or said assay-performance-substance; incubating said composition to form a complex which includes a particle and said labeled component; magnetically collecting said complex at the surface of an electrode; inducing said label to luminesce by contacting it with a trigger, said trigger being formed in-situ by conversion of a precursor molecule upon introduction of electrochemical energy; and measuring the emitted luminescence to measure the presence of the analyte of interest in the sample.

20 Claims, 7 Drawing Sheets

U.S. PATENT DOCUMENTS

| | | |
|---|---|---|
| 4,447,546 | 5/1984 | Hirschfeld. |
| 4,480,042 | 10/1984 | Craig et al.. |
| 4,515,890 | 5/1985 | Manderino et al.. |
| 4,539,507 | 9/1985 | VanSlyke et al.. |
| 4,554,088 | 11/1985 | Whitehead et al.. |
| 4,628,037 | 12/1986 | Chagnon et al.. |
| 4,652,333 | 3/1987 | Carney. |
| 4,652,533 | 3/1987 | Jolley. |
| 4,661,444 | 4/1987 | Li. |
| 4,677,067 | 6/1987 | Schwartz et al.. |
| 4,695,392 | 9/1987 | Whitehead et al.. |
| 4,695,393 | 9/1987 | Whitehead et al.. |
| 4,698,302 | 10/1987 | Whitehead et al.. |
| 4,731,337 | 3/1988 | Luotola et al.. |
| 4,745,077 | 5/1988 | Holian et al.. |
| 4,777,145 | 10/1988 | Luotola et al.. |
| 4,865,997 | 9/1989 | Stoker. |
| 4,916,081 | 4/1990 | Kamada et al.. |
| 4,945,045 | 7/1990 | Forrest et al.. |
| 4,978,610 | 12/1990 | Forrest et al.. |
| 5,115,534 | 5/1992 | Fournier. |

FOREIGN PATENT DOCUMENTS

| | | |
|---|---|---|
| 89/04854 | of 0000 | WIPO. |
| WO 85/00663 | 2/1985 | WIPO. |
| 85/01253 | 3/1985 | WIPO. |
| WO 86/05815 | 10/1986 | WIPO. |
| 87/00987 | 2/1987 | WIPO. |
| 8707386 | 3/1987 | WIPO. |
| 87/06706 | 11/1987 | WIPO. |
| 88/03947 | 6/1988 | WIPO. |
| 89/01814 | 3/1989 | WIPO. |
| WO 89/04373 | 5/1989 | WIPO. |
| 89/04915 | 6/1989 | WIPO. |
| 89/04919 | 6/1989 | WIPO. |
| 90/01370 | 2/1990 | WIPO. |
| 89/04859 | 5/1990 | WIPO. |

OTHER PUBLICATIONS

Casadei J, Powell MJ, Kenten JH. Expression and secretion of aequorin as a chimeric antibody using a mammalian expression vector. *Proc. Natl. Acad. Sci.* 1990; 87:2047–51.

Coutlee F, Bobo L, Mayur K, Yolken RH, Viscidi RP. Immunodetection of DNA with biotinylated RNA probes: A study of reactivity of a monoclonal antibody to DNA–RNA hybrids. *Anal. Biochem.* 1989; 181:96–105.

Devices, Japanese Journal of Applied Physics, vol. 18, No. 7, 1979, 1295–1301.

Dulbecco, R., and Freeman, G., (1959) *Virology* B, 398.

Dynal, Dynabeads, M–450, Dynal A.S. Oslo, Norway, Product Literature. No Date Supplied.

Ege, et al., J. Anal. Chem. 1984, 56, 2413.

Faulkner, L.R. et al., J.Am. Chem. Soc. 94, 691 (1972).

Hamblen, et al., "Characteristics of an Electrically Controlled Fluorescent Dye Panel", IEEE Conference Record of 1972, Conference on Display Devices, Oct. 11–12, (1972).

Hemingway, et al., "Electrogenerated Chemiluminescence. XXI. Energy Transfer from an Exciplex to a Rare Earth Chelate", J. Am. Chem. Soc. 1975, 97: 1, 200–01.

Heney, G. and Orr, G.A. (1981) *Anal. Biochem.* 114, 92–96.

Iscove, N.N. and Melchers, F., *J. Experimental Medicine* 147, 923–933, 1978.

Itaya, et al., "Electrogenerated Chemiluminescence with Solvated Electrons in Hexamethylphosphoramide. 2", J. Am. Chem. Soc. 1978, 100: 19, 5996–6002.

Keszthelyi, et al., "Electrogenerated Chemiluminescence. XV. On the Formation of Excimers and Exciplexes in ECL", Chemical Physics Letters 1974, vol. 24, No. 2, 300–04.

Keszthelyi, et al., "Electrogenerated Chemiluminescence. XIV. Effect of Supporting Electrolyte Concentration and Magnetic Field Effects in the 9, 10–Dimethylanthracene–tri–p–tolylamine in Tetrahydrofuran", Chemical Physics Letters 1973, vol. 23, No. 2, 219, 220–22.

Kohen et al., "Chemiluminescence & Bioluminescence Immunoassay", Alternative Immunoassays, W.P. Collins, (1985) John Wiley & Sons, Ltd., Chap. 8, pp. 103–109.

Ludvik, et al., J. Electroanal. Chem. 1986, 215, 179.

Lyons J, Janssen JWG, Bartram C, Layton M, Mufti GJ. Mutation of Ki–ras and N–ras oncogenes in myelodysplastic syndromes. *Blood* 1988; 71:1707–12.

Lytle, et al., Photochem. Photobiol. 1971, 13, 123.

Maloy, et al., "Electrogenerated Chemiluminescence. II. The Rotating–Ring Disk Electrode and the Pyrene–N,N,N', N'–Tetramethyl–p–phenylenediamine System", J. Phys. Am. Chem. 1968, vol. 72, No. 12, 4348–50.

Marmur, J. (1961) *J. Mol. Biol.* 3, 208.

Mullis KB, Faloona FA. Specific synthesis of DNA in vitro via a polymerase–catalyzed chain reaction. *Methods Enzymol* 1987; 155:335–50.

Ngo TT. Procedure for activating polymers with primary and/or secondary hydroxyl groups. *Makromol Chem. Macromol Symp.* 1988; 17:224–39.

Noffsigner, et al., Anal Chem. 1987, 59, 865.

Pragst, et al., "Electrogenerated Chemiluminescence in Mechanistic Investigations of Electroorganic Reactions, Part I. Cathodic Cleavage of Bis–(2,4,5–Triphenylimidazolyl)–1,2 (Dilophyl)," J. Electroanal. Chem. 1980, 112, 339.

Pragst, et al., J. Electroanal. Chem. 1986, 197, 245.

Reddy EP, Reynolds RK, Santo E, Barbacid M. A point mutation is responsible for the acquisition of the transforming properties by the T24 humanbladder carcinoma oncogene. *Nature* 1982; 300:149–52.

Rozhitskii, et al., "Steady–State Electrochemiluminescence in Solutions with Organometallic Electrolytes", J. Appl. Spectrosc. 1978, vol. 28, No. 2, 197–202.

Rubenstein, et al., "Electrogenerated Chemiluminescent Determination of Oxylate", Anal. Chem. 1983, 54, 9, 1580–82.

Rubinstein, et al., J. Am. Chem. Soc. 1981, 103, 512.

Saiki RK, Gelfand DH, Stoffel S, Scharf SJ, Higuchi R, Horn GT, Mullis KB, Erlich HA. Primer–directed amplification of DNA with a thermostable DNA polymerase. *Science* 1988; 239:487–91.

Sato, et al., "Quenching Of Fluorescence in Europium B–Diketone Chelate Solutions and Its Application to Display Devices", Japanese J. of Appl. Physics, vol. 18, No. 7, pp. 1295–1301, Jul. 1979.

Shibata DK, Arnheim N, Martin JW. Detection of human papilloma virus in paraffin–embedded tissue using the polymerase chain reaction. *J. Exp. Med.* 1988; 167:225–30.

Smith, J.D., Freeman, G., Vogt, M., and Dulbecco, R., (1960), *Virology* 12, 155.

Tachikawa, et al., "Electrogenerated Chemiluminescence. Effect on a Magnetic Field on the Delayed Fluorescence and ECL of Several Systems Involving Excimers or Exciplexes", Chemical Physics Letters 1974, vol. 26, No. 4, 568–73.

Tachikawa, et al., "Electrogenerated Chemiluminescence XII. Magnetic Field Effects on ECL in the Tetracene–TMPD System; Evidence for Triplet–Triplet Annihilation of Tetracene", Chemical Physics Letters 1973, vol. 19, No. 2, 287–89.

Tissue Culture Standards Committee, *In Vitro* 5:2, 93, No Date Supplied.

Tokel-Takvoryan, et al., "Electrogenerated Chemiluminescence. XIII. Electrochemical and Electrogenerated Chemiluminescence Studies of Ruthenium Chelates", J. Am. Chem. Soc. 1973, 95: 20, 6582–89.

Updyke TV, Nicolson GL. Immunoaffinity isolation of membrane antigens with biotinylated monoclonal antibodies and streptavidin–agarose. *Methods Enzymol* 1986; 121:717–25.

Weetall, H.H. and Hotaling, T., Biosensors 3 (1987/88), 57–63.

Wheeler, et al., "A Silicon Phthalocyanine and a Silicon Naphthalocyanine: Synthesis, Electrochemistry, and Electrogenerated Chemiluminescence", J. Am. Chem. Soc. 1984, 106, 7404–10.

Wilson, et al., "Electrogenerated Chemiluminescence of trans–Stilbene Derivatives", J. Electrochem. Soc.: Electrochemical Science and Technology (1981), vol. 128, No. 10, 2085–89.

Yanofsky, C. et al. (1981) *Nucleic Acids Res.* 24, 6647–6668.

Yee C, Krishnan–Hewlett I, Baker CC, Schlegel R, Howly PM. Presence and Expression of Human Papillomavirus sequences in human cervical carcinoma cell lines. *Am. J. Pathol.* 1985; 199:361–6.

Ziebig, et al., "Intramolecular Exciplexes in the Electrogenerated Chemiluminescence of 1–Amino–3–Anthryl–(9)–Propanes", *Journal of Luminescence 21* (1980), 353–66.

5,746,974

APPARATUS FOR IMPROVED LUMINESCENCE ASSAYS USING PARTICLE CONCENTRATION, ELECTROCHEMICAL GENERATION OF CHEMILUMINESCENCE AND CHEMILUMINESCENCE DETECTION

This application is a division of application Ser. No. 08/348,749, filed Dec. 1, 1994, now abandoned [Curtis, Morris & Safford docket No. 370068-3480, entitled Methods and Apparatus for Improved Luminescence Assays Using Particle Concentration, Electrochemical Generation of Chemiluminescence Detection] which is a continuation of application Ser. No. 07/728,093, filed Jul. 10, 1991 now abandoned, which is a continuation in part of application Ser. No. 07/652,427, filed Feb. 6, 1991 now abandoned, which in turn is a continuation in part of application Ser. No. 07/539,389, filed Jun. 18, 1990 now abandoned, which is a continuation of Ser. No. 07/266,882, filed Nov. 3, 1988 now abandoned.

FIELD OF THE INVENTION

This application relates generally to methods and apparatus for conducting binding assays, more particularly to those which measure the presence of an analyte of interest by measuring luminescence emitted by one or more labeled components of the assay system. More specifically, the invention relates to precise, reproducible, accurate homogeneous or heterogeneous specific binding assays of improved sensitivity in which the luminescent component is concentrated in the assay composition and collected before being caused to chemiluminesce.

BACKGROUND OF THE INVENTION

Numerous methods and systems have been developed for the detection and quantitation of analytes of interest in biochemical and biological substances. Methods and systems which are capable of measuring trace amounts of microorganisms, pharmaceuticals, hormones, viruses, antibodies, nucleic acids and other proteins are of great value to researchers and clinicians.

A very substantial body of art has been developed based upon the well known binding reactions, e.g., antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials. Of particular interest are labels which can be made to luminesce through photochemical, chemical, and electrochemical means. "Photoluminescence" is the process whereby a material is induced to luminesce when it absorbs electromagnetic radiation. Fluorescence and phosphorescence are types of photoluminescence. "Chemiluminescent" processes entail the creation of luminescent species by chemical transfer of energy. "Electrochemiluminescence" entails creation of luminescent species electrochemically.

Chemiluminescent assay techniques where a sample containing an analyte of interest is mixed with a reactant labeled with a chemiluminescent label have been developed. The reactive mixture is incubated and some portion of the labeled reactant binds to the analyte. After incubation, the bound and unbound fractions of the mixture are separated and the concentration of the label in either or both fractions can be determined by chemiluminescent techniques. The level of chemiluminescence determined in one or both fractions indicates the amount of analyte of interest in the biological sample.

In such techniques, the incubated sample is exposed to a voltammetric working electrode in order to trigger luminescence. In the proper chemical environment, such electrochemiluminescence is triggered by a voltage impressed on the working electrode at a particular time and in a particular manner. The light produced by the label is measured and indicates the presence or quantity of the analyte. For a fuller description of such electrochemiluminescent techniques, reference is made to PCT published application US85/01253 (W086/02734), PCT published application number US87/00987, and PCT published application U.S. 88/03947. The disclosures of the aforesaid applications are incorporated by reference.

It is desirable to carry out chemiluminescent assays without the need for a separation step during the assay procedure and to maximize the signal modulation at different concentrations of analyte so that precise and sensitive measurements can be made.

Among prior art methods for separation assays are those such as described in U.S. Pat. No. 4,141,687 and European Patent Application 0,030,087 which relate to magnetically separating particles in a conduit after which the particles are removed to a separate chamber for analysis of the label.

Among prior art methods for nonseparation assays are those which employ microparticulate matter suspended in the assay sample to bind one or more of the binding components of the assay.

U.S. Pat. No. 4,305,925 relates to the detection and determination of clinically relevant proteins and peptides by means of nephelometric and turbidimetric methods. The methods disclosed involve binding the antigen or antibody to latex particles which perform the function of light scattering or adsorption.

U.S. Pat. No. 4,480,042 relates to techniques employing particle reagents consisting of shell-core particles. The shell contains functional groups to which compounds of biological interest can be covalently bonded, and the high refractive index of the core results in high sensitivity to light scattering measurements. The technique is based upon agglutination reactions which result from the reaction of bivalent antibodies with multivalent antigens of interest to produce aggregates which can be detected and/or measured in various ways.

U.S. Pat. No. 4,419,453 likewise relates to the use of colored latex agglutination test methods useful for detecting the presence of immunochemicals such as antibodies and immunogens.

Based upon this prior art, it would not have appeared possible to use microparticulate matter in assays wherein a luminescent phenomenon is measured. One would expect that the luminescence from free chemiluminescent moieties would be absorbed, scattered, or otherwise suffer interference from the microparticulate matter.

Contrary to that expectation, U.S. application Ser. No. 266,882 (PCT published application U.S. 89/04919) teaches sensitive, specific binding assay methods based on a luminescent phenomenon wherein inert microparticulate matter is specifically bound to one of the binding reactants of the assay system. The assays may be performed in a heterogeneous (one or more separation steps) assay format and may be used most advantageously in a homogeneous (nonseparation) assay format.

U.S. 89/04919 relates to a composition for an assay based upon a binding reaction for the measurement of luminescent phenomenon, which composition includes a plurality of suspended particles having a surface capable of binding to a component of the assay mixture. In another aspect, it is directed to a system for detecting or quantitating an analyte of interest in a sample, which system is capable of conducting the assay methods using the assay compositions of the inventions. The system includes means for inducing the label compound in the assay medium to luminesce, and means for measuring the luminescence to detect the presence of the analyte of interest in the sample.

Thus, U.S. 89/04919 is directed to methods for the detection of an analyte of interest in a sample, which method includes the steps of (1) forming a composition comprising (a) a sample suspected of containing an analyte of interest, (b) an assay-performance-substance selected from the group consisting of (i) analyte of interest or analog of the analyte of interest, (ii) a binding partner of the analyte of interest or its said analog, and (iii) a reactive component capable of binding with (i) or (ii), wherein one of said substances is linked to a label compound having a chemical moiety capable of being induced to luminesce, and (c) a plurality of suspended particles capable of specifically binding with the analyte and/or a expect that the luminescence from free chemiluminescent moieties would be absorbed, scattered, or otherwise suffer interference from the microparticulate matter.

Contrary to that expectation, U.S. application Ser. No. 266,882 (PCT published application U.S. 89/04919) teaches sensitive, specific binding assay methods based on a luminescent phenomenon wherein inert microparticulate matter is specifically bound to one of the binding reactants of the assay system. The assays may be performed in a heterogeneous (one or more separation steps) assay format and may be used most advantageously in a homogeneous (nonseparation) assay format.

U.S. 89/04919 relates to a composition for an assay based upon a binding reaction for the measurement of luminescent phenomenon, which composition includes a plurality of suspended particles having a surface capable of binding to a component of the assay mixture. In another aspect, it is directed to a system for detecting or quantitating an analyte of interest in a sample, which system is capable of conducting the assay methods using the assay compositions of the inventions. The system includes means for inducing the label compound in the assay medium to luminesce, and means for measuring the luminescence to detect the presence of the analyte of interest in the sample.

Thus, U.S. 89/04919 is directed to methods for the detection of an analyte of interest in a sample, which method includes the steps of (1) forming a composition comprising (a) a sample suspected of containing an analyte of interest, (b) an assay-performance-substance selected from the group consisting of (i) analyte of interest or analog of the analyte of interest, (ii) a binding partner of the analyte of interest or its said analog, and (iii) a reactive component capable of binding with (i) or (ii), wherein one of said substances is linked to a label compound having a chemical moiety capable of being induced to luminesce, and (c) a plurality of suspended particles capable of specifically binding with the analyte and/or a substance defined in (b)(i), (ii), or (iii); (2) incubating the composition to form a complex which includes a particle and said label compound; (3) inducing the label compound to luminesce; and (4) measuring the luminescence emitted by the composition to detect the presence of the analyte of interest in the sample. Those same methods may be used to quantify the amount of analyte in a sample by comparing the luminescence of the assay composition to the luminescence of a composition containing a known amount of analyte.

Analogs of the analyte of interest, which may be natural or synthetic, are compounds which have binding properties comparable to the analyte, but include compounds of higher or lower binding capability as well. Binding partners suitable for use in the present invention are well-known. Examples are antibodies, enzymes, nucleic acids, lectins, cofactors and receptors. The reactive components capable of binding with the analyte or its analog and/or with a binding partner thereof may be a second antibody or a protein such as Protein A or Protein G or may be avidin or biotin or another component known in the art to enter into binding reactions.

Advantageously, the luminescence arises from electrochemiluminescence (ECL) induced by exposing the label compound, whether bound or unbound to specific binding partners, to a voltametric working electrode. The ECL reactive mixture is controllably triggered to emit light by a voltage impressed on the working electrode at a particular time and in a particular manner to generate light. Although the emission of visible light is an advantageous feature the composition or system may emit other types of electromagnetic radiation, such as infrared or ultraviolet light, X-rays, microwaves, etc. Use of the terms "electrochemiluminescence," "electrochemiluminescent," "luminescence," "luminescent," and "luminesce" includes the emission of light and other forms of electromagnetic radiation.

The methods taught in U.S. 89/04919 permit the detection and quantitation of extremely small quantities of analytes in a variety of assays performed in research and clinical settings. The demands of researchers and clinicians makes it imperative, however, to lower the detection limits of assays performed by these methods to increase the sensitivities of those assays and to increase the speed at which they can be performed.

Various methods are known in the art for increasing the signal from labeled species by concentrating them before subjecting them to a measurement step. In U.S. Pat. No. 4,652,333, for example, particles labeled with fluorescent, phosphorescent or atomic fluorescent labels are concentrated by microfiltration before a measurement step is performed.

It is also known in the art to concentrate labeled immunochemical species prior to a measurement step, by, e.g., drawing magnetically responsive labeled particles to the surface of a measurement vessel. In U.S. Pat. Nos. 4,1731, 337, 4,777,145, and 4,115,535, for example, such particles are drawn to the vessel wall and then are irradiated to excite a fluorophoric emission of light.

In U.S. Pat. No. 4,945,045, particles are concentrated on a magnetic electrode. An electrochemical reaction takes place at the electrode facilitated by a labeled chemical mediator. The immunochemical binding reaction alters the efficiency of the mediator resulting in a modulated signal when binding takes place.

OBJECTS OF THE INVENTION

It is therefore a primary object of this invention to provide homogeneous (non-separation) and heterogeneous (separation) methods, reagents and apparatus, for the conduct of binding assays.

It is a further object of this invention to provide non-separation, specific binding assays, reagents and apparatus, based upon the measurement of chemiluminescence emitted from an assay composition containing microparticulate matter.

It is a further and related object to provide such assays, reagents and apparatus having improved sensitivity, faster assay time, greater sensitivity, lower detection limits and greater precision than has heretofore been achieved.

DESCRIPTION OF THE INVENTION

Definition of Terms

Chemiluminescence is defined as a luminescence reaction in which the energy responsible for generating the high-energy excited state of a molecule is derived from an energetic chemical reaction. A chemiluminescent reaction thus involves the direct conversion of chemical energy to electromagnetic radiation (ultraviolet, visible, or infrared radiation). Luminescence occurs when the excited-state molecule returns to its ground-state energy level, emitting a photon having a particular wavelength which is characteristic of the molecule and the energy of its excited state relative to its ground-state.

Energy is generated by many chemical reactions; such reactions are called exothermic reactions. In most cases the energy appears as heat and induces vibrational, rotational, and translational energy in the molecule. In a chemiluminescence reaction at least part of this energy is channeled into the formation in the high-energy excited state. This generally requires a highly energetic and rapid reaction of two molecules, one of which is capable of luminescence emission:

$$A+B \rightarrow C^*+D$$

$$C^* \rightarrow C+h\nu$$

The quantity hv represents a photon of electromagnetic radiation. h is Planck's constant and ν is the frequency of the emitted light.

In some chemiluminescent reactions the electronic energy of the excited-state molecule C* is transferred to another molecule, $$C^*+E \rightarrow C+E^*$$

which then decays to its ground-state by emitting a photon of electromagnetic radiation, $$E^* \rightarrow E+h\nu.$$

Specific binding assays, e.g. immunoassays, using chemiluminescent detection use one of the reactants as a label attached to one of the binding partners. In such assays, the reactants are generally called the label and the trigger and react according to the equation:

Label+Trigger→Label*+By-products

Label*→By-products+hν

Examples of chemiluminescent labels which have been used in specific binding assays include acridinium esters, luminol, isoluminol, oxalate esters, dioxetanes, and luciferin. In many cases, the trigger molecule is an oxidant such as hydrogen peroxide which is capable of oxidizing the label in a highly energetic reaction which is capable of generating the excited state of the label.

Enhancer molecules are sometimes used in chemiluminescent reactions as a means of increasing the efficiency of the chemiluminescence process. Such molecules generally slow the reaction rate of the reaction and increase the quantum yield of the light emission.

Chemiluminescent binding assays have also been demonstrated in which an enzyme is used as the label. In these cases, the enzyme catalyzes the chemiluminescent reaction in the presence of a trigger solution. An example is the use of the enzyme horseradish peroxidase to catalyze the chemiluminescent reaction of luminol in the presence of hydrogen peroxide and hydroxide ion.

The term "chemiluminescent moiety," "label," "label compound," and "label substance," are used interchangeably. It is within the scope of the invention for the species termed "chemiluminescent moiety," "label compound," "label substance" and "label" to be linked to molecules such as an analyte or an analog thereof, a binding partner of the analyte or an analog thereof, and further binding partners of such aforementioned binding partner, or a reactive component capable of binding with the analyte, an analog thereof or a binding partner as mentioned above. The above-mentioned species can also be linked to a combination of one or more binding partners and/or one or more reactive components. Additionally, the aforementioned species can also be linked to an analyte or its analog bound to a binding partner, a reactive component, or a combination of one or more binding partners and/or one or more reactive components. It is also within the scope of the invention for a plurality of the aforementioned species to be bound directly, or through other molecules as discussed above, to an analyte or its analog. For purposes of brevity, these ligands are referred to as an assay-performance-substance.

The terms detection and quantitation are referred to as "measurement", it being understood that quantitation may require preparation of reference compositions and calibrations.

The terms collection and concentration of complex may be used interchangeably to describe the concentration of complex within the assay composition and the collection of complex at, e.g., an electrode surface of a flow cell.

BRIEF DESCRIPTION OF THE INVENTION

Figure 1:
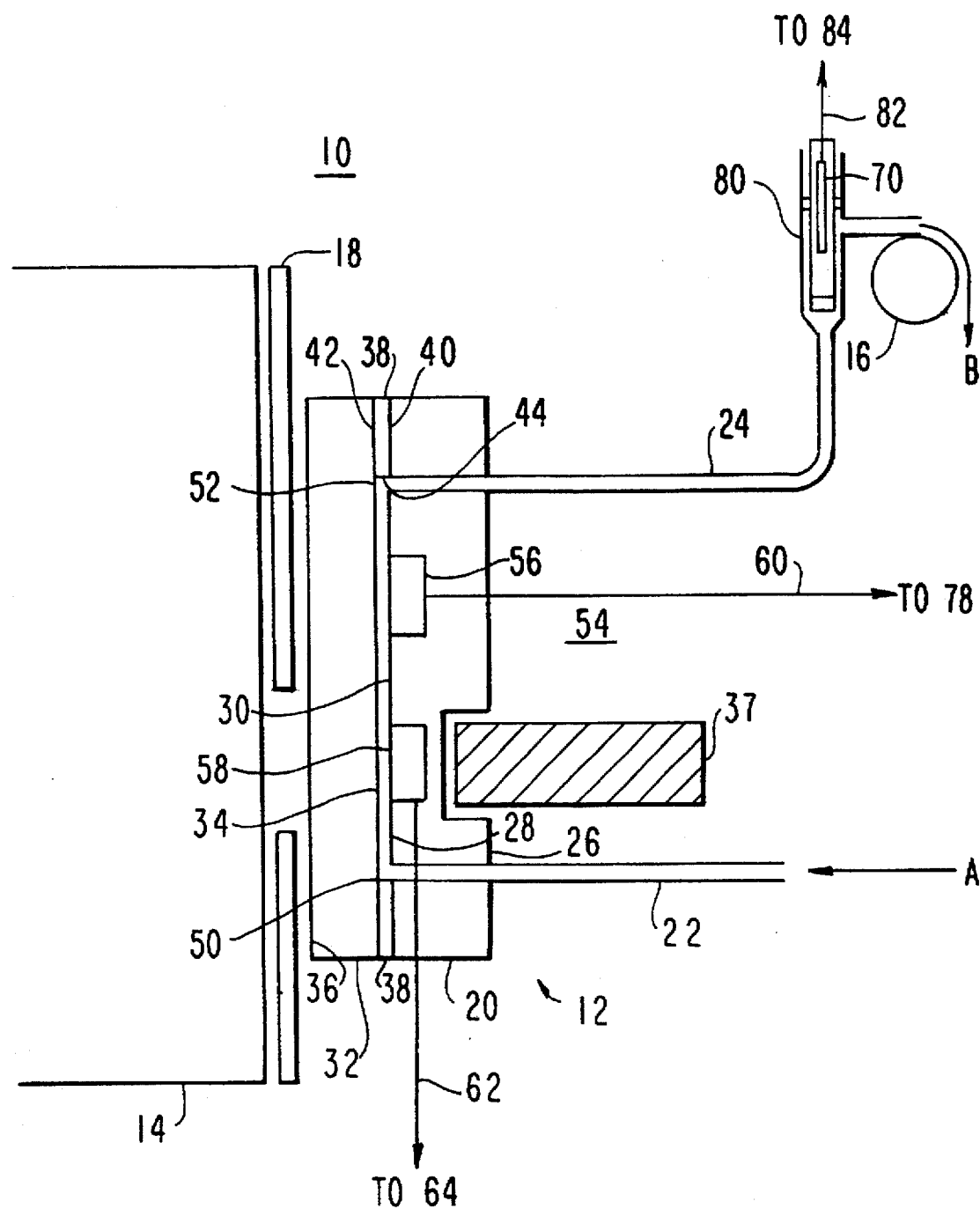
FIG. 1 is a schematic drawing of a cell including a permanent magnet for performing the microparticulate-based nonseparation and separation assays of the invention.

In its broadest embodiment, the invention is in a method for performing a binding assay for an analyte of interest present in a sample. The steps include:
 (a) forming a composition containing
  (i) said sample
  (ii) an assay-performance-substance which contains a component linked to a label compound capable of chemiluminescing when triggered and
  (iii) a plurality of particles capable of specifically binding with the analyte and/or said assay-performance-substance;
 (b) incubating said composition to form a complex which includes a particle and said labeled component;
 (c) collecting said complex at the surface of an electrode;
 (d) inducing said label compound to luminesce by contacting it with a trigger, said trigger being formed in-situ by conversion of a precursor molecule upon introduction of electrochemical energy, for example by imposition of a voltage on said electrode; and
 (e) measuring the emitted luminescence to measure the presence of the analyte of interest in the sample.

Preferably, the trigger is an oxidant capable of oxidizing the label such that the label is oxidized and chemiluminesces. Also preferably, the particles are magnetically responsive and the complex is magnetically collected at the surface of the electrode.

The complex may be collected on, e.g., an electrode surface where it is excited and induced to chemiluminesce, as by introducing into a collection zone an oxidant capable of oxidizing the label such that the label is oxidized and chemiluminesces. According to the present invention, the oxidant is formed in situ by conversion of a precursor molecule. The composition containing the sample may also contain the precursor molecule, or the precursor molecule may be introduced before incubating, after incubating but before magnetically collecting, or after magnetically collecting the incubated complex.

Thus, the present invention relates to a method for performing a binding assay for an analyte of interest present in a sample including the steps of:
 (a) forming a composition containing
  (i) said sample,
  (ii) an assay-performance-substance which contains a component linked to a label compound capable of chemiluminescing when oxidized,
  (iii) a plurality of coated magnetic particles capable of specifically binding with the analyte and/or said assay-performance-substance, and
  (iv) a molecule capable of being electrochemically converted to an oxidant capable of oxidizing said label;
 (b) incubating said composition to form a complex which includes a particle and said label compound;
 (c) magnetically collecting said complex at the surface of an electrode;
 (d) converting said molecule to said oxidant by imposing a voltage on said electrode, such that said label is oxidized and luminesces; and
 (e) measuring the emitted luminescence to measure the presence of the analyte of interest in the sample.

The present invention further relates to a method for performing a binding assay for an analyte of interest present in a sample including the steps of:
 (a) forming a composition containing
  (i) said sample
  (ii) an assay-performance-substance which contains a component linked to a label compound capable of chemiluminescing when oxidized, and
  (iii) a plurality of coated magnetic particles capable of specifically binding with the analyte and/or said assay-performance-substance;
 (b) introducing to said composition a molecule capable of being electrochemically converted to an oxidant capable of oxidizing said label;
 (c) incubating said composition to form a complex which includes a particle and said label compound;
 (d) magnetically collecting said complex at the surface of an electrode;
 (e) converting said molecule to said oxidant by imposing a voltage on said electrode, such that said label is oxidized and luminesces; and
 (f) measuring the emitted luminescence to measure the presence of the analyte of interest in the sample.

The present invention further relates to a method for performing a binding assay for an analyte of interest present in a sample including the steps of:
 (a) forming a composition containing
  (i) said sample,
  (ii) an assay-performance-substance which contains a component linked to a label compound capable of chemiluminescing when oxidized, and
  (iii) a plurality of coated magnetic particles capable of specifically binding with the analyte and/or said assay-performance-substance;
 (b) incubating said composition to form a complex which includes a particle and said label compound;
 (c) introducing to said composition a molecule capable of being electrochemically converted to an oxidant capable of oxidizing said label;
 (d) magnetically collecting said complex at the surface of an electrode;
 (e) converting said molecule to said oxidant by imposing a voltage on said electrode, such that said label is oxidized and luminesces; and
 (f) measuring the emitted luminescence to measure the presence of the analyte of interest in the sample.

The present invention even further relates to a method for performing a binding assay for an analyte of interest present in a sample including the steps of:
 (a) forming a composition containing
  (i) said sample
  (ii) an assay-performance-substance which contains a component linked to a label compound capable of chemiluminescing when oxidized, and
  (iii) a plurality of coated magnetic particles capable of specifically binding with the analyte and/or said assay-performance-substance;
 (b) incubating said composition to form a complex which includes a particle and said label compound;
 (c) magnetically collecting said complex at the surface of an electrode;
 (d) introducing to said composition a molecule capable of being electrochemically converted to an oxidant capable of oxidizing said label;
 (e) converting said molecule to said oxidant by imposing a voltage on said electrode, such that said label is oxidized and luminesces; and
 (f) measuring the emitted luminescence to measure the presence of the analyte of interest in the sample.

While the invention is preferably carried out by collecting the complex in a measurement zone, i.e., on a surface which converts the precursor molecule to the oxidant, the invention also embraces methods wherein the complex is collected in a measurement zone and thereafter means are brought to that zone or other steps taken to induce and measure luminescence.

The collection of the complex may be carried out by several different methods, including gravity settling, filtration, centrifugation and magnetic attraction of magnetically responsive particles which form part of the complex. The several embodiments are described in further detail below.

While batch assays can be performed, continuous or semi-continuous assays can be performed in flow cells. In a flow cell, the solid-phase remains in the measurement cell while the solution flows through and exits the cell. If the solid-phase (e.g., particles) are more dense than water, i.e., have a density greater than that of water, (more than 1.0 g/mL) the force of gravity upon the particles causes them to fall to the bottom of the cell. The cell can be constructed such that the particles settle to the bottom as the fluid flows through the cell or the cell can be constructed such that the majority of the sample is contained in the cell in a columnar compartment above the working electrode of a chemiluminescent system. Sufficient dwell time in the cell must be provided to permit the particles to settle on the surface of the electrode before inducing chemiluminescence.

In another embodiment of the invention, the assay composition containing suspended particles having a density greater than the balance of the assay composition may be subjected to centrifugation in order to remove the particles to a measurement zone where they are subsequently brought into contact with, e.g., a trigger to induce chemiluminescence, or brought directly into contact with an electrode in the centrifugation step.

In this embodiment, the measurement cell is provided with means to rapidly rotate the sample and sample enclosure. Centrifugal force causes the particles in the sample to move outward from the axis of rotation of the sample enclosure and to collect on the outer surface of the sample enclosure. The outer surfaces of such sample enclosure may constitute the working electrode of a chemiluminescent measurement system.

In a third embodiment, the particles may be removed by filtration from the assay composition. In this embodiment the particles need not have a density greater than the balance of the assay composition. The invention, the particles are separated from the solution and concentrated by drawing the solution through a filter, e.g. pumping and collecting the particles on the surface of the filter. This surface of the filter is, for example, coated with a thin metal film which can serve as the working electrode in a chemiluminescent detection system.

In a preferred embodiment, the suspended particles are magnetically responsive, e.g. they may be paramagnetic or ferromagnetic, and are collected in a measurement zone or, preferably, directly at the surface of an electrode, by imposition of a magnetic field on the particles. The measurement cell is equipped with a magnet. The magnetic field of the magnet applies a force on the particles as they reside in a batch cell or as they flow through a flow cell, causing them to separate from the bulk of the solution onto the surface of the cell which is in closest proximity to the magnet. If the magnet is placed in a proper orientation and in close proximity to the working electrode of a chemiluminescent detection system the particles will concentrate on the surface of the working electrode.

Several different heterogeneous and homogeneous formats for binding assays can be implemented using the methods described above to collect and concentrate the complex on the surface of an electrode. In a heterogeneous binding assay the complex is separated from the composition before measuring luminescence from the label. In homogeneous assays, no separation of the bound (to the solid phase) and unbound labeled reagents is made.

In a homogeneous assay, when the complex is concentrated on the surface of the working electrode, the measured signal from the label is much greater than it would be in the absence of a collection step. The signal from the uncomplexed labeled reagents, in contrast, is not changed. Hence, despite the presence of the uncomplexed labeled reagents in the measurement cell, the signal from the collected complex is stronger than in an assay without collection of complex. The detection limit for the binding assay is, much improved as a result of the collection procedure.

In a preferred embodiment of the invention, an in-situ separation step is included in the homogeneous binding assay procedure. After the assay composition, i.e., sample, assay performance substance and particles have been pumped into the measurement cell and the complex captured upon the working electrode, a second fluid is pumped through the cell which is free of label or labeled reagents, thereby performing an in-situ wash or separation of the complex from unbound components of the assay composition. This assay procedure is technically a heterogeneous binding assay. However, the ability to perform the separation inside the measurement cell is advantageous in that it does not require additional separation apparatus and the procedure is generally much faster than external separation methods.

Heterogeneous binding assays are conducted using the invention by mixing the components of the assay composition and allowing them to react for a predetermined length of time. The assay composition is then subjected to a separation step wherein the solution is separated from the particles. Chemiluminescence is then measured from either the complex or the solution. Measuring the chemiluminescence from the complex after a concentration step permits measurement of analyte with better accuracy and with a lower detection limit than is possible without concentration.

DETAILED DESCRIPTION OF THE INVENTION

The invention, as well as other objects and features thereof, will be understood more clearly and fully from the following description of certain preferred embodiments.

The invention is broadly applicable to analytes of interest which are capable of entering into binding reactions. These reactions include, e.g., antigen-antibody, ligand receptor, DNA and RNA interactions, and other known reactions. The invention relates to different methods and assays for qualitatively and quantitatively detecting the presence of such analytes of interest in a multicomponent sample.

The Samples

The sample which may contain the analyte of interest, which may be in solid, emulsion, suspension, liquid, or gas form, may be derived from, for example, cells and cell-derived products, water, food, blood, serum, hair, sweat, urine, feces, tissue, saliva, oils, organic solvents or air. The sample may further comprise, for example, water, acetonitrile, dimethyl sulfoxide, dimethyl formamide, n-methyl-pyrrolidone or alcohols or mixtures thereof.

The Analytes

Typical analytes of interest are a whole cell or surface antigen, subcellular particle, virus, prion, viroid, antibody, antigen, hapten, fatty acid, nucleic acid, protein, lipoprotein, polysaccharide, lipopolysaccharide, glycoprotein, peptide, polypeptide, cellular metabolite, hormone, pharmacological agent, synthetic organic molecule, organometallic molecule, tranquilizer, barbiturate, alkaloid, steroid, vitamin, amino acid, sugar, lectin, recombinant or derived protein, biotin, avidin, streptavidin, or inorganic molecule present in the sample. Typically, the analyte of interest is present at a concentration of $10^{-3}$ molar or less, for example, as low as $10^{-12}$ molar or lower.

Assay-Performance-Substance

The assay-performance-substance which is combined with the sample containing the analyte of interest contains at least one substance selected from the group consisting of (i) added analyte of interest or its analog, as defined above, (ii) a binding partner of the analyte of interest or its said analog, and (iii) a reactive component, as defined above, capable of binding with (i) or (ii), wherein one of said substances is linked to a compound or moiety, e.g. a chemiluminescent moiety capable of being induced to luminesce. The labeled substance may be a whole cell or surface antigen, a subcellular particle, virus, prion, viroid, antibody, antigen, hapten, lipid, fatty acid, nucleic acid, polysaccharide, protein, lipoprotein, lipopolysaccharide, glycoprotein, peptide, polypeptide, cellular metabolite, hormone, pharmacological agent, tranquilizer, barbiturate, alkaloid, steroid, vitamin, amino acid, sugar, nonbiological polymer (preferably soluble), lectin, recombinant or derived protein, synthetic organic molecule, organometallic molecule, inorganic molecule, biotin, avidin or streptavidin. In one embodiment, the reagent is a chemiluminescent moiety conjugated to an antibody, antigen, nucleic acid, hapten, small nucleotide sequence, oligomer, ligand, enzyme, or biotin, avidin, streptavidin, Protein A, Protein G, or complexes thereof, or other secondary binding partner capable of binding to a primary binding partner through protein interactions.

Analogs of the analyte of interest, which can be natural or synthetic, are typically compounds which have binding properties comparable to the analyte, but can also be compounds of higher or lower binding capability. The reactive components capable of binding with the analyte or its analog, and/or with a binding partner thereof, and through which the chemiluminescent moiety can be linked to the analyte, is suitably a second antibody or a protein such as Protein A or Protein G, or avidin or biotin or another component known in the art to enter into binding reactions.

The function of the chemiluminescent moieties is to emit electromagnetic radiation as a result of introduction into the reaction system of a trigger, particularly an oxidant. In order to do this, they must be capable of being stimulated to an excited energy state and also capable of emitting electromagnetic radiation, such as a photon of light, upon descending from that excited state.

The trigger is formed in-situ by conversion of a precursor molecule, for example water, to an oxidant, for example hydrogen peroxide or superoxide, upon introduction of electrochemical energy, for example by imposition of a voltage waveform on an electrode. As a second example, oxygen molecules as the precursor are electrochemically reduced to form hydrogen peroxide, the trigger.

The amount of chemiluminescent moiety incorporated in accordance with the invention will vary from system to system. Generally, the amount of such moiety utilized is that amount which is effective to result in the emission of a detectable, and if desired, quantitatable, emission of electromagnetic energy, from the aforementioned composition or system. The detection and/or quantitation of an analyte of interest is typically made from a comparison of the luminescence from a sample containing an analyte of interest and a chemiluminescent moiety to the luminescence emitted by a calibration standard developed with known amounts of the analyte of interest and chemiluminescent moiety. This assumes a homogeneous format. In the heterogeneous mode, a separation as discussed previously is carried out prior to chemiluminescent analysis.

As can be appreciated by one of ordinary skill in the art, the identity and amount of the chemiluminescent moiety will vary from one system to another, depending upon prevailing conditions. The appropriate chemiluminescent moiety, and sufficient amount thereof to obtain the desired result, can be determined empirically by those of ordinary skill in the art, once equipped with the teachings herein, without undue experimentation.

The Particles

The particles advantageously comprise microparticulate matter having a diameter of 0.05 um to 200 um, preferably 0.1 um to 100 um, most preferably 0.5 um to 10 um, and a surface component capable of binding to the analyte and/or one or more of the other substances defined in subparagraphs (a)(i), (a)(ii), or (a)(iii) above. For example, the microparticulate matter may be crosslinked starch, dextrans, cellulose, proteins, organic polymers, styrene copolymer such as styrene/butadiene copolymer, acrylonitrile/butadiene/styrene copolymer, vinylacetyl acrylate copolymer, or vinyl chloride/acrylate copolymer, inert inorganic particles, chromium dioxide, oxides of iron, silica, silica mixtures, and proteinaceous matter, or mixtures thereof. Desirably, the particles are suspended in the chemiluminescent system.

Assay Media

In order to operate a system in which an electrode introduces electrochemical energy to convert the precursor molecule to the oxidant such that said label is oxidized and luminesces, it is necessary to provide an electrolyte in which the electrode is immersed and which contains the precursor molecule. The electrolyte is a phase through which charge is carried by ions. Generally, the electrolyte is in the liquid phase, and is a solution of one or more salts or other species in water, an organic liquid or mixture of organic liquids, or a mixture of water and one or more organic liquids. However, other forms of electrolyte are also useful in certain embodiments of the invention. For example, the electrolyte may be a dispersion of one or more substances in a fluid—e.g., a liquid, a vapor, or a supercritical fluid—or may be a solution of one or more substances in a solid, a vapor or supercritical fluid.

The electrolyte is suitably a solution of a salt in water. The salt can be a sodium salt or a potassium salt preferably, but incorporation of other cations is also suitable in certain embodiments, as long as the cation does not interfere with the chemiluminescent interaction sequence. The salt's anion may be a phosphate, for example, but the use of other anions is also permissible in certain embodiments of the invention—once again, as long as the selected anion does not interfere with the chemiluminescent interaction sequence.

The composition may also be nonaqueous. While supercritical fluids can in certain instances be employed advantageously, it is more typical to utilize an electrolyte comprising an organic liquid in a nonaqueous composition. Like an aqueous electrolyte, the nonaqueous electrolyte is also a phase through which charge is carried by ions. Normally, this means that a salt is dissolved in the organic liquid medium. Examples of suitable organic liquids are acetonitrile, dimethylsulfoxide (DMSO), dimethylformamide (DMF), methanol, ethanol, and mixtures of two or more of the foregoing. Illustratively, tetraalkylammonium salts, such as tetrabutylammonium tetrafluoroborate, which are soluble in organic liquids can be used with them to form nonaqueous electrolytes.

The electrolyte is, in certain embodiments of the invention, a buffered system. Phosphate buffers are often advantageous. Examples are an aqueous solution of sodium phosphate/sodium chloride, and an aqueous solution of sodium phosphate/sodium fluoride.

Apparatus for Measuring Chemiluminescence

Figure 2:
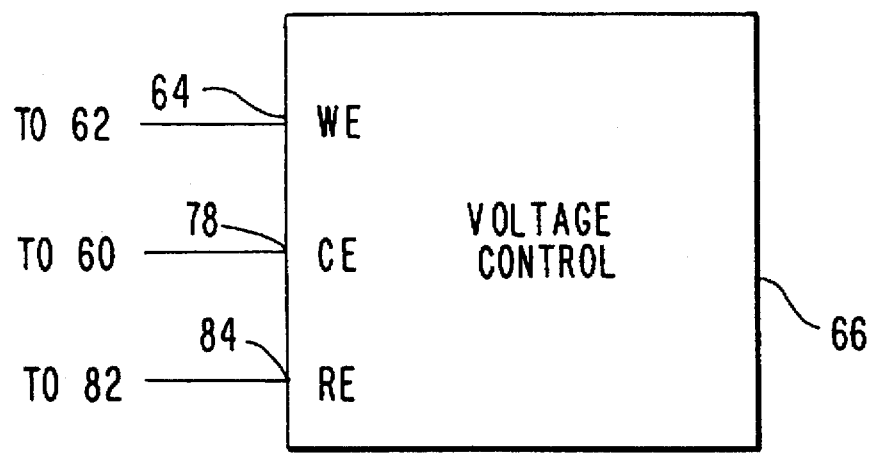
FIG. 2 is a simplified diagram of a voltage control apparatus for use with the cell of FIG. 1.

An apparatus for carrying out the assays of the invention is described in FIGS. 1 and 2. FIG. 1 discloses an advantageous chemiluminescent apparatus, but the methods of the present invention are not limited to application in apparatus 10, but rather may be employed in other types of chemiluminescent apparatus which include a working electrode or other triggering surface to provide electrochemical energy to convert the precursor to the trigger and a means for collecting a labeled component. While the methods of the invention can be carried out in a static or flow-through mode, apparatus 10 includes a flow-through cell, which provides distinct advantages for many types of samples including binding assay samples. Further details of apparatus for carrying out the chemiluminescent assays of the invention are disclosed in commonly assigned published PCT applications US 89/04854 and U.S. 90/01370.

Apparatus 10 includes an electrochemical cell 12, a light detection/measurement device 14, which may advantageously be a photomultiplier tube (PMT), photodiode, charge coupled device, photographic film or emulsion or the like, and a pump 16, which is advantageously a peristaltic pump, to provide for fluid transport to, through and from cell 12. Alternatively, a positive displacement pump may be used. A shutter mechanism 18 is provided between cell 12 and PMT 14 and is controllably operated to open only so far as to expose PMT 14 to cell 12 during chemiluminescent measurement periods. The shutter mechanism may be closed, for example, during maintenance. Also included in apparatus 10 but not illustrated in FIG. 1 is a lightproof housing intended to mount the various components therein and to shield PMT 14 from any external light during the chemiluminescent measurements.

Cell 12 itself includes a first mounting block 20 through which passes an inlet tube 22 and an outlet tube 24, which may be advantageously constructed of Plexiglas. Mounting block 20 has a first, outer surface 26 and a second, inner surface 28 defining one side of a sample-holding volume 30 of cell 12 in which cell 12 holds the cleaning and/or conditioning and/or measurement solutions during corresponding operations of apparatus 10. Inlet and outlet tubes 22, 24 pass through mounting block 20 from outer surface 26 to inner surface 28 and open into sample-holding volume 30. A second mounting block 32 is advantageously constructed of a material which is substantially transparent at the wavelength of chemiluminescent light emitted by the chemiluminescent moiety. Mounting block 32 is therefore advantageously formed of glass, plastic, quartz or the like and has a first, outer surface 34 and a second, inner surface 36. Second mounting block 32 is separated from first mounting block 20 by an annular spacer 38, advantageously constructed of Teflon or other non-contaminable material. Thus, outer surface 34 of mounting block 30 defines the second side of the sample-holding volume 30. Spacer 38 has an outer portion 40 and a central aperture 42 whose inner edge 44 defines the side wall of sample-holding volume 30. Outer portion 40 seals the inner surface 28 of first mounting block 20 to outer surface 34 of second mounting block 32 to prevent any solution from passing out from sample-holding volume 30 between the two surfaces 28, 34.

Inlet tube 22 intersects sample-holding volume 30 at a first end 50 thereof adjacent to spacer 38 and outlet tube 24 intersects sample-holding volume 30 at a second end 52 thereof, adjacent spacer 38. The combination of inlet tube 22, sample-holding volume 30 and outlet tube 24 thereby provides a continuous flow path for the narrow, substantially laminar flow of a solution to, through and from cell 12.

Mounted on inner surface 28 of first mounting block 20 is an electrode system 54, which, in the illustrated embodiment, includes working electrode 58. In other embodiments, two or more working electrodes may advantageously be provided. Working electrode 58 is where the electrochemical and chemiluminescent reactions of interest can take place. Working electrode 58 is a solid voltammetric electrode and may therefore be advantageously constructed of platinum, gold, carbon or other materials which are effective for this purpose. Wire connector 62 connected to working electrode 58 passes out through first mounting block 20.

Connector 62 is connected to a first, "working electrode" terminal 64 of a voltage control 66, illustrated in FIG. 2. Voltage control 66 advantageously operates in the manner of a potentiostat to supply voltage signals to working electrode 58 and optionally to measure current flowing therefrom during a chemiluminescent measurement.

The potentiostat operation of voltage control 66 is further effected through a counter electrode 56 and, optionally but advantageously, a reference electrode 70. Counter electrode 56 and working electrode 58 provide the interface to impress the potential on the solution within sample-holding volume 30 which energizes the chemical reactions and triggers electrochemical conversion of precursor to trigger in the sample and/or provides energy for cleaning and conditioning the surfaces of cell 12. Counter electrode 56 is connected by a wire connector 60 to a second, "counter electrode" terminal 78 of voltage control 66.

Reference electrode 70 provides a reference voltage to which the voltage applied by the working electrode 58 is referred, for example, +1.2 volts versus the reference. Reference electrode 70 is advantageously located in outlet tube 24 at a position 80 spaced from cell 12 and is connected through a wire connector 82 to a third "reference electrode" terminal 84 of voltage control 66. In the three electrode mode, current does not flow through reference electrode 70. Reference electrode 70 may be used in a three electrode mode of operation to provide a poised, known and stable voltage and is therefore advantageously constructed of silver/silver chloride (Ag/AgCl) or is a saturated calomel electrode (SCE). Voltage control 66 may be operable in a two electrode mode of operation using only working electrode 58 and electrode 56 as a counter/reference electrode. In this two electrode mode of operation, counter/reference electrode 56 is electrically connected to voltage control terminals 78 and 84 on voltage control 66. In this case, voltage control 66 operates essentially as a battery. Voltage control 66 supplies voltage signals to working and counter electrodes 58 and 56 and optionally measures the current flowing through the respective electrodes. Reference electrode 70 may alternatively be a so-called "quasi-reference" electrode constructed of platinum, gold, stainless steel or other material, which provides a less stable voltage, yet one that is measurable with respect to the solution in contact. In both the two and three electrode mode, the reference electrode 70 or 56 serves the purpose of providing a reference against which the voltage applied to working electrodes 58 is measured. The poised voltage reference is currently considered to be more advantageous. Voltage control 66 in its potentiostat operation controls the various electrodes by providing a known voltage at working electrode 58 with respect to reference electrode 70 while measuring the current flow between working electrode 58 and counter electrode 56. Potentiostats for this purpose are well known, and the internal structure of voltage control 66 may therefore correspond to any of the conventional, commercially available potentiostats which produce the above-recited functions and so do not form a part of the present invention per se. Indeed, apparatus 10 may alternatively be constructed without an internal voltage control 66, and may be adapted to be connected to an external potentiostat which is separately controlled for providing the required voltage signals to electrodes 56, 58, and 70. These voltage signals, applied in a specific manner as described below, provide repeatable initial conditions for the surfaces of working electrode 58 and advantageously for the surfaces of cell 12 as a whole, a feature which contributes significantly to improved precision in chemiluminescent measurements.

Pump 16 is advantageously positioned at outlet tube 24 to "pull" solution from a sample volume in the direction of arrow A into inlet tube 22. The solution will flow through inlet tube 22, sample-holding volume 30 and outlet tube 24 past reference electrode 70 and out in the direction of arrow B. Alternatively, pump 16 may be positioned at inlet tube 22 to "push" the solution through apparatus 10. Advantageously, this same flow path through inlet tube 22, sample-holding volume 30 and outlet tube 24 is used for all solutions and fluids which pass through cell 12, whereby each fluid performs a hydrodynamic cleaning action in forcing the previous fluid out of cell 12. Pump 16 may be controlled to suspend its operation to hold a particular solution in cell 12 for any period of time.

The flow-through construction of apparatus 10 permits working electrodes to be impressed with a variable voltage or to be continuously held at a preoperative potential while being continuously exposed to one or more solutions without exposing working electrode 58 (or counter and reference electrodes 56, 70) to air. Exposure to air, which opens the circuit to the reference electrode 70, permits unknown, random voltage fluctuations which destroy the reproducibility of surface conditions on working electrode 58. The flow-through construction permits the rapid alternation between initializing steps, in which electrode system 54 is cleaned and conditioned, and measurement steps, in which one or more measurement waveforms or sweeps trigger chemiluminescent.

The invention is also directed to reagent compositions. Broadly, the reagent compositions may be any one of the components of the assay systems of the invention, i.e., (a) electrolyte, (b) label compound containing a chemiluminescent moiety, (c) particles, including magnetically responsive particles, (d) analyte of interest or an analog of the analyte of interest, (e) a binding partner of the analyte of interest or of its analog, (f) a reactive component capable of reacting with (d) or (e), (g) a trigger precursor molecule, or (h) a chemiluminescence-reaction enhancer. The reagents may be combined with one another for convenience of use, i.e., two component, three component, and higher multiple component mixtures may be prepared, provided that the components are not reactive with one another during storage so as to impair their function in the intended assay. Desirably, the reagents are two-component or multicomponent mixtures which contain particles as well as one or more other components.

The invention is also directed to kits. The kits may include vessels containing one or more of the components (a) to (h) recited above or the kits may contain vessels containing one or more reagent compositions as described above comprising mixtures of those components, all for use in the assay methods and systems of the invention.

DESCRIPTION OF PREFERRED EMBODIMENTS OF THE INVENTION

While a wide range of particles can be employed in the particle-based assays of the invention, generally the particles have a density of from 1.0 to 5.0 g/mL and preferably have a density of from 1.1 to 2 g/mL. Choice of the optimum density is within the skill of the art, the rate of settling in gravity-driven assays being a trade-off between the speed of the assay and the desire to create a uniform layer of complex on the electrode surface.

Particles having a wide range of mean diameters can also be employed. Particles having a mean diameter of from 0.001 to 100 μm can be used and preferably the particles have a mean diameter of from 0.01 to 10 μm.

Wide ranges of concentration of particles in the assay composition can also be employed. For example, the concentration can range from 1 to 10,000 μg/mL to preferably from 5 to 1000 μg/mL. Desirably, the density of the particles, their size and their concentration is selected such that the particles settle at a rate of at least 0.5 mm/min and preferably at a faster rate.

In the filtration mode of performing the invention, the filtration means desirably has a pore size, measured as mean diameter, from broadly 0.01 to 90% of the mean diameter of the particles and preferably from 10% to 90% of that diameter.

The art has described a number of magnetic particles which can be used in the assays of the invention. For example, U.S. Pat. No. 4,628,037, 4,695,392, 4,695,393, 4,698,302, 4,554,088, U.K. Patent Application GB 2,005, 019A and EP 0,180,384, describe a variety of magnetic particles which can be used with success. The particles may be paramagnetic or ferromagnetic and may be coated with various materials to which binding compounds are coupled so that the magnetic particle can be used in immunoassays. Desirably the magnetic particles used in the invention have a susceptibility of at least 0.001 cgs units and desirably the susceptibility is at least 0.01 cgs units. The magnetic particles may have a broad range of densities, i.e. from substantially less than that of water, 0.01, to 5 g/mL and preferably from 0.5 to 2 g/mL. The particle sizes can range from 0.001 to 100 μm and preferably from 0.01 to 10 μm. The concentration of the particles may range broadly from 1 to 10,000 μg per mL and preferably is from 5 to 1000 μg per mL.

Desirably the magnetic particles which are used have a low magnetic remanence, as described for example EP 0,180,384, so that after the magnetic field is removed from the electrode surface, the particles demagnetize and can be swept out of the assay cell. Desirably the density, concentration and particle size of the magnetic particles is chosen such that the settling time is at least 0.5 mm/min and desirably it is above that rate. In operation of the magnetic cell it is often desirable to remove the magnet means from the electrode surface prior to inducing electrochemiluminescence in order not to interfere with the operation of the photomultiplier tube.

Assays

A variety of assays can be performed using the methods of the invention.

Figure 3:
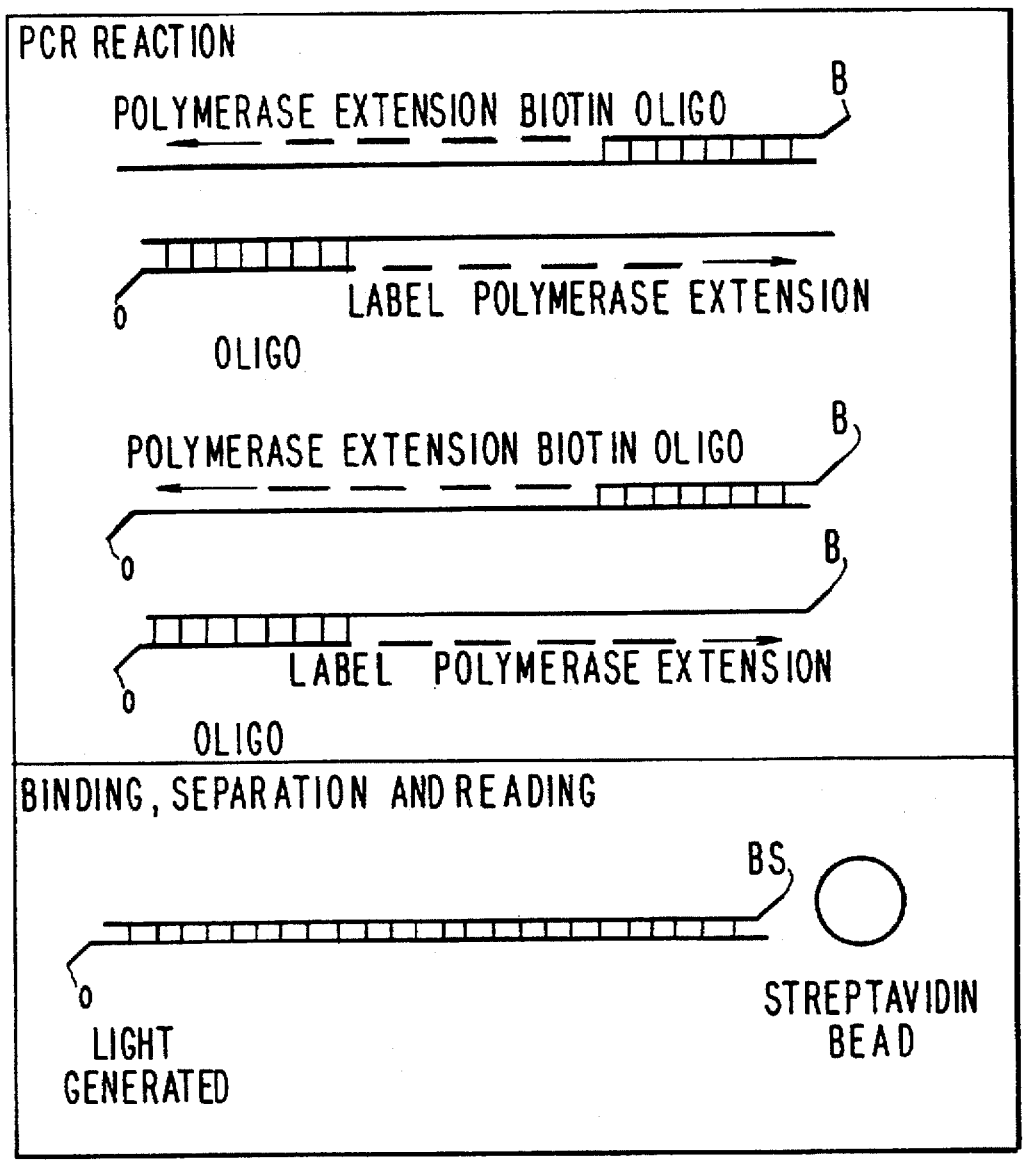
FIG. 3 is a schematic representation of a direct incorporation PCR format using chemiluminescent labeled oligonucleotides and biotin chemiluminescent labeled oligonucleotides as primers.

An assay is performed as shown in FIG. 3. The PCR products resulting from the reaction are labeled with biotin and a chemiluminescent label. Streptavidin beads capture the bifunctionalized DNA via biotin streptavidin binding and this is followed by washing. The bead bound product is then subjected to analysis detecting the chemiluminescent label.

Figure 4:
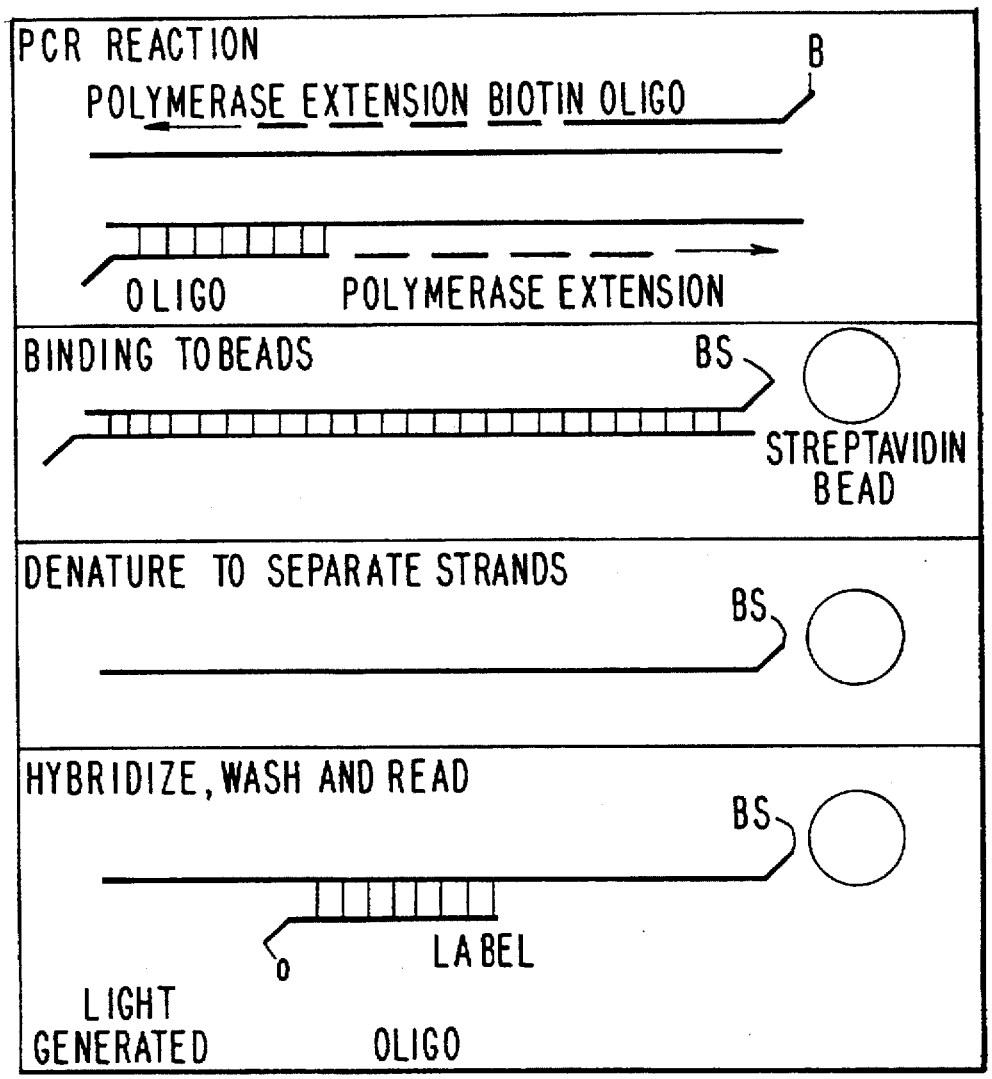
FIG. 4 is a schematic representation of a normal PCR format using a biotinylated primer to allow the generation of biotinylated PCR and PRODUCT.

An assay is performed as shown in FIG. 4. The biotinylated PCR product is captured on streptavidin beads and the non-biotinylated strand removed. The bead bound PCR product is then hybridized with a chemiluminescent labeled oligonucleotide. This is followed by chemiluminescent analysis to detect the label.

Figure 5:
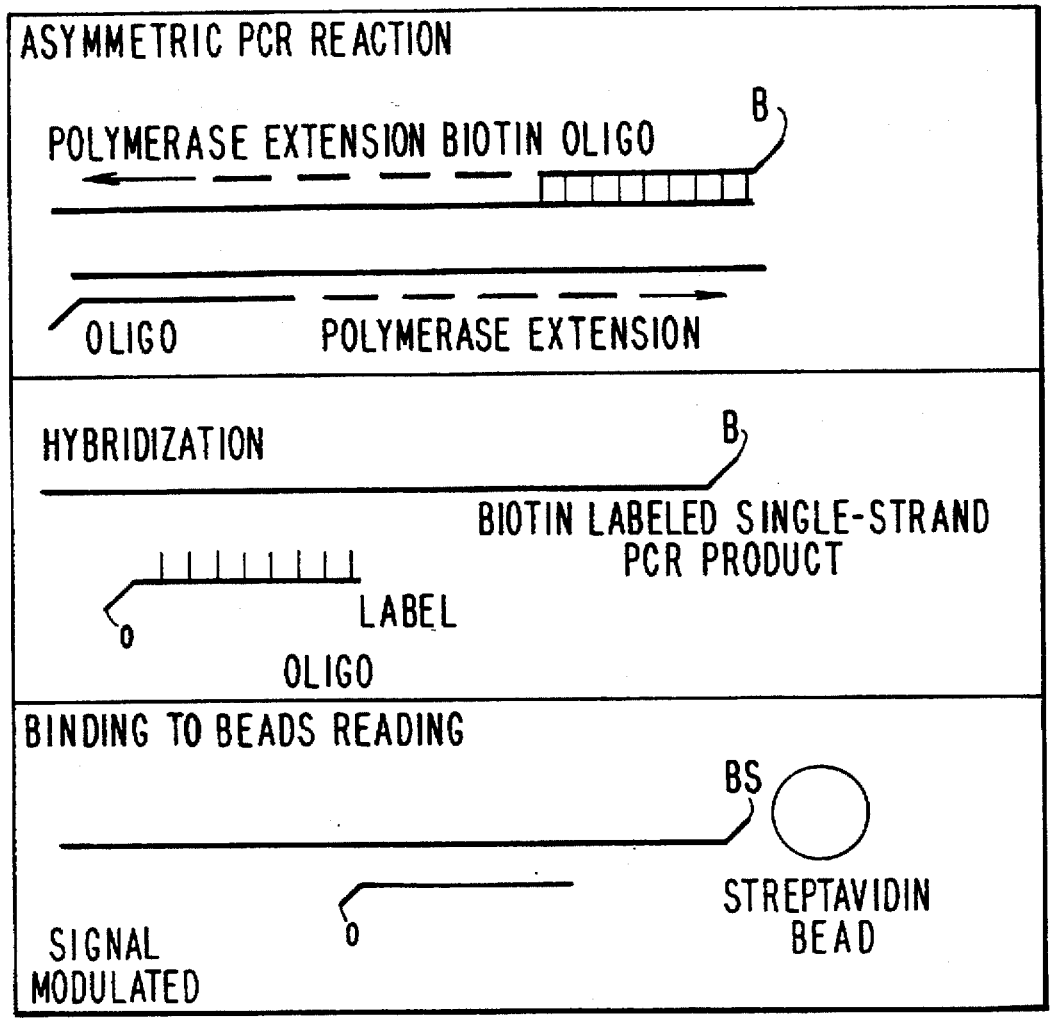
FIG. 5 is a schematic representation of an asymmetric PCR assay format generating single-stranded biotinylated DNA for later hybridization to chemiluminescent labeled oligonucleotides.

An assay is conducted as shown in FIG. 5. The hybrids are captured on streptavidin beads. This is followed by chemiluminescent analysis without washing.

EXAMPLES

Instrumentation, Materials, and Methods (1) Instrumentation

A flow-through apparatus, employing three electrodes, as described in FIGS. 1 and 2, was used.

Working Electrode—Au disk, 3 mm diameter

Counter Electrode—Au disk, 3 mm diameter

Reference Electrode—Ag/AgCl

Teflon Gasket (0.015" thick)

Plexiglas Faceplate

Inlet Tubing=0.042" id polypropylene

Aspiration Rates: variable from 0.01 to 5 mL/min

Potentiostat: microprocessor controlled Luminometer using Hamamatsu R374 PMT (low gain red sensitive tube); PMT Voltage variable 0–1400 V

EXAMPLE 1

Apparatus and Method for Collection of Microparticles by Gravity

Figure 6:
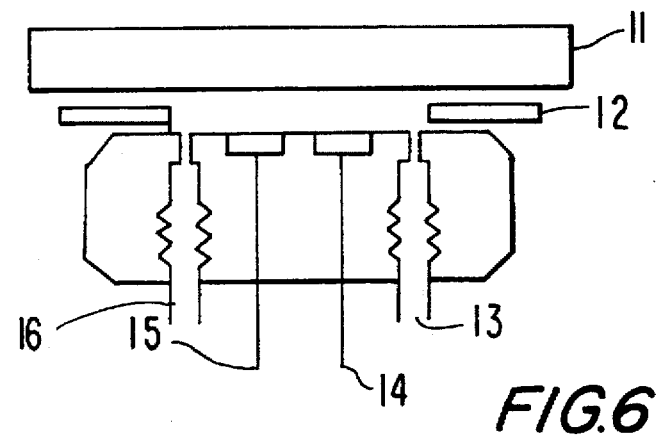
FIG. 6 is a schematic representation of an assay cell used to conduct assays relying upon gravitational force to cause the complex to settle.

The measurement is conducted in a cell as shown in FIG. 6. Reference is made to FIG. 6 which depicts an apparatus for conducting an assay using the force of gravity. The components of the apparatus include a transparent window identified by reference numeral 11, a gasket identified by reference numeral 12, a block which includes an inlet 13, a working electrode 14, a counterelectrode 15 and an outlet port 16. The plane of the cell block is horizontal, i.e. perpendicular to the direction of the earth's gravitational field. Labeled microparticles (Dynal) in a buffer are drawn to the cell by means of a peristaltic pump. The pump is turned off after the particles reach the cell. The microparticles in the cell chamber fall onto the working electrode surface. The rate of fall of microparticles is determined to be approximately constant at 0.5 mm/min over a distance of 10 mm. The number of particles to settle is a function of time and rate of fall. The chemiluminescent intensity is proportional to the number of particles that settle on the working electrode. The number of particles that reach the surface, and therefore the chemiluminescent intensity, is limited by the height of fluid sample over the working electrode.

EXAMPLE 2

Figure 7:
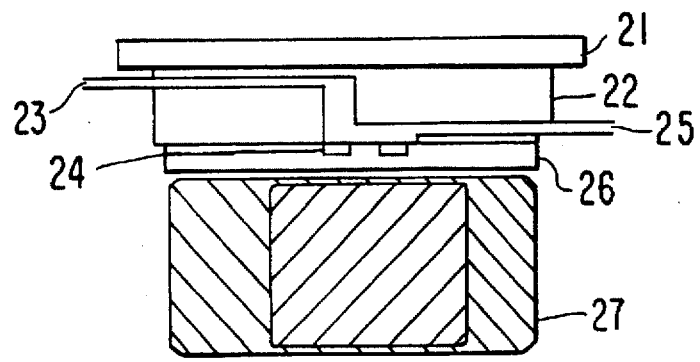
FIG. 7 is a schematic representation of a sedimentation assay cell which employs an electromagnet to cause the complex to settle on the electrode surface.

Chemiluminescent Apparatus and Method for Deposition of Microparticles
Magnetic Collection using a Sedimentation Cell A cell for conduct of an assay using magnetic force to cause the microparticulate to settle is shown in FIG. 7. Reference numeral 21 refers to a transparent window, reference numeral 22 to a gasket, reference numeral 23 to the inlet in the cell block, reference numeral 24 to the working electrode, reference numeral 25 to the sample outlet, reference numeral 26 to the cell block itself and reference 27 to an electromagnet.

The plane of the cell block is oriented horizontally. Labeled microparticles (Dynal) in buffer are drawn to the cell by means of a peristaltic pump. The pump is turned off after the microparticles reach the cell. The microparticles in the cell chamber are drawn to the working electrode by means of a magnetic field generated using electromagnet 27 operating at 12 volts and 1.5 amps. By application of the electromagnet, the rate of deposition of microparticles is greatly increased over that observed when the microparticles settle solely due to the force of gravity.

EXAMPLE 3

Chemiluminescent Apparatus and Method for Deposition of Microparticles
Magnetic Collection using a Collection Cell An assay is carried out in a cell as described in FIG. 1. With reference to FIG. 1, reference numeral 32 refers to transparent window, reference numeral 38 to a gasket, reference numeral 22 to an inlet in the cell block, reference numeral 58 to a working electrode, reference numeral 35 to the cell block itself, reference numeral 24 to the sample outlet and reference numeral 37 to a permanent magnet.

The plane of the cell block is oriented horizontally. Labeled microparticles (Dynal) in chemiluminescent buffer are drawn to the electrochemical cell by means of a peristaltic pump. Prior to the sample introduction, permanent magnet 37 is positioned immediately below the working electrode/solution interface at a distance of 0.035 inches. As the sample is being drawn to the cell, the microparticles collect in a collection zone, for example deposit onto an area over the working electrode, as defined by the area of the magnet. The pump is turned off and the magnet withdrawn after the entire sample is deposited. The longer the collection time, the more particles are deposited. Increasing the concentration of particles on the working electrode results in an increased chemiluminescent intensity.

EXAMPLE 4

Use of Magnet for Deposition of Microparticles
Magnetic Field Orientation

Figure 8B:
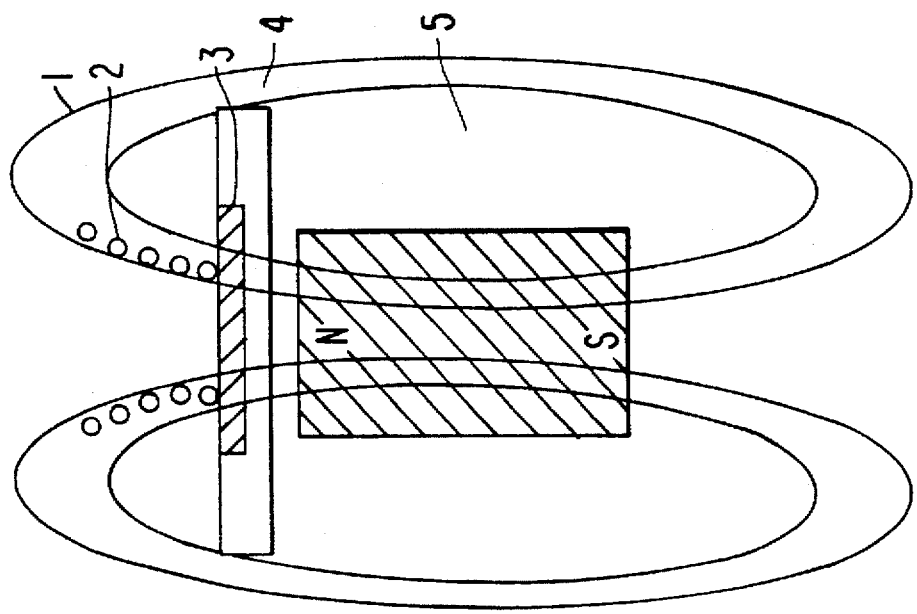
FIG. 8(A–B) is a schematic representation of the lines of force in the vicinity of the electrode surface as a function of the orientation of the magnet beneath the electrode surface.
Figure 8A:
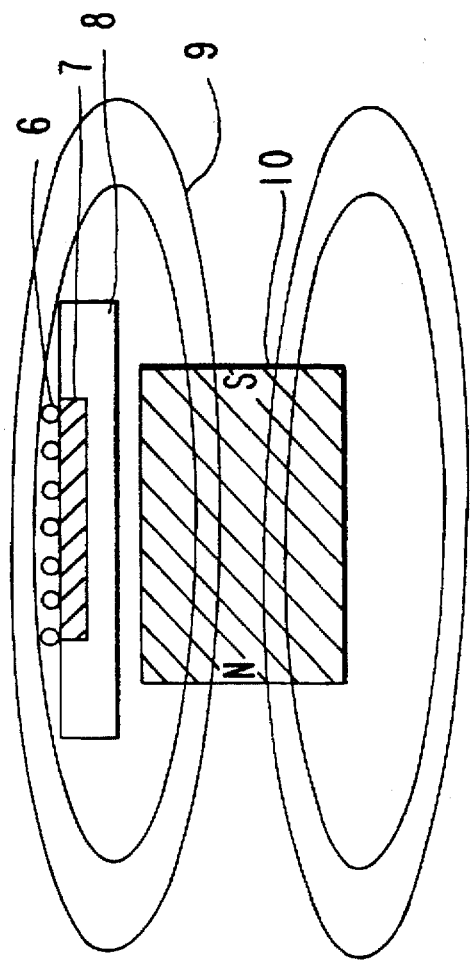

Microparticles which are attracted to a magnet whether a permanent magnet or electromagnet, align with the orientation of the magnetic field. FIG. 8 depicts magnetic fields and the resultant particle arrangements which are parallel (A) and perpendicular (B) to the surface of the working electrode, in the vicinity of that surface. One skilled in the art will appreciate that the orientation of the particles in the collection zone will affect the efficiency of subsequent contact with trigger.

EXAMPLE 5

Particle Collection and Concentration by Filtration

Microparticles which are magnetically responsive, non-magnetically responsive, and of a wide range of densities can advantageously be collected by filtration upon the surface of a membrane filter. In one embodiment of the invention, the particles are pumped through a portion of a filter membrane which has pore sizes which are smaller than the diameter of the particles but preferably are substantially smaller than the particle diameter and at a sufficiently high surface density such that the collection of particles will not cause blockage of the pores. The filter is advantageously largely transparent such that the filter, after collection of the particles, can be placed upon the surface of a working electrode for the purpose of converting a precursor to a trigger to induce chemiluminescence from the particles and measuring the luminescence to measure the quantity of chemiluminescent label on the particles.

In another embodiment, the membrane filter having pore sizes as described above is attached or placed upon the surface of an absorbent material such that capillarity or "wicking" will spontaneously draw fluids containing microparticles through the membrane filter without requiring any apparatus to induce the flow of fluid through the filter.

In the preferred embodiment, the membrane filter, having pore sizes as described above, is coated with a thin film of metal or other electronically conductive material such that the surface of the membrane can serve as a working electrode in the chemiluminescent apparatus. The conductive films are readily applied to the surface of a membrane by methods commonly used in the fabrication of microelectronic devices, e.g., thermal evaporation or sputtering.

Such a filter-electrode is readily mounted in a flow cell such that the flow-path for the fluid is through the filter-electrode. Particles in the stream are trapped by the filter-electrode and are easily washed in-situ providing for a rapid and simple means for performing heterogeneous assays without any external washing apparatus.

EXAMPLE 6

Particle Collection and Concentration by Centrifugal Method

Figure 9:
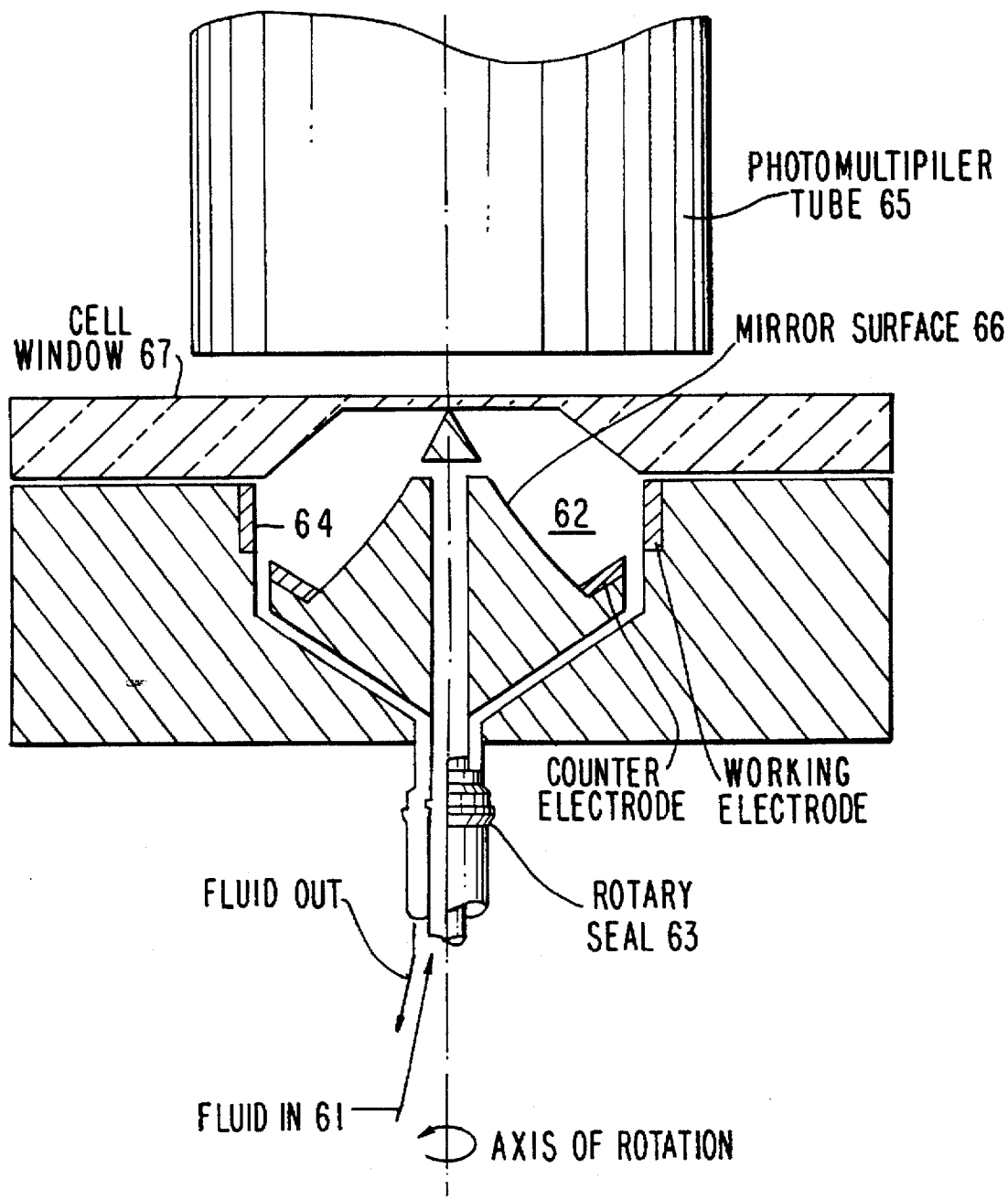
FIG. 9 is a schematic representation of a rotary flow cell wherein the complexes are deposited upon the surface of the electrode by centrifugation.

The rotary flow cell shown in FIG. 9 provides another means to collect the complex on the surface of the working electrode in order to measure luminescence. The assay solution 61 is pumped into cell 62 through rotary seal 63 while a rotational motion is imparted to the cell. The denser particles of the complex are concentrated on the surface of working electrode 64. While the cell is still rotating the solution passes out of the cell. The light output passing through cell window 67 is measured by photomultiplier tube 65. The light output is directed from the vertical working electrode surface 64 reflecting off curved mirror surface 66 located at the center of the cell. The cell is then flushed and cleaned for the next cycle. This may be accomplished with the cell stopped or rotating.

EXAMPLE 7

Coating of Particles With Labeled Non-specific Protein at Moderate Surface Concentration 30 mg (1 ml) of 4.5 um uncoated magnetically responsive, polystyrene M-450 DYNABEADS (DYNAL, Oslo, Norway) are washed by magnetic separation with a 150 mM phosphate buffer pH 7.5 solution using 2 ml/wash. 150 µg of acridinium ester-labeled antibody (London Diagnostics LumaTag TSH Labeled Antibody) in 1 ml of phosphate buffer saline (PBS) with 0.05% thimerasol is added to the particles. This mixture is allowed to incubate overnight at room temperature with agitation. The solution is then magnetically separated from the particles and the fluid removed. To block unreacted sites, 1 ml of 3% BSA/PBS with 0.05% sodium azide is added to the particles, and the resultant solution is allowed to incubate 2 hours at room temperature. The particles are washed 5 times (2 ml/wash), and then finally resuspended in 6 ml of the same buffer for storage.

EXAMPLE 8

Chemiluminescent Measurement Using Magnetically Responsive Particles

Magnetically responsive particles (Dynal, Oslo, Norway) are coated with labeled proteins as described in Example 7. The coated particles are washed with phosphate buffer three times before making 2 mL of a 30 ug/mL suspension in pH 4, 100 mM carbonate/bicarbonate buffer. Using a peristaltic pump, 500 ul of the particle suspension is drawn into the flow cell (Example 2). As the particles flow to the working electrode, they are attracted and concentrated onto the working electrode by a magnet. After the particles are magnetically collected, a solution of 0.25N NaOH is drawn through the cell. The chemiluminescence is generated by conversion of precursor molecules to trigger molecules by one of three methods:

(1) a potential waveform is applied to the electrochemical electrodes such that water (precursor) is oxidized, forming hydrogen peroxide and other oxidizing species (triggers) at the working electrode. The hydrogen peroxide or other oxidizing species triggers the chemiluminescent reaction of the acridinium ester label.

(2) a potential waveform is applied to the electrochemical electrodes such that oxygen (precursor) dissolved in the solution is reduced to form hydrogen peroxide (trigger) according to the equation

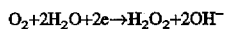

$$O_2 + 2H_2O + 2e^- \rightarrow H_2O_2 + 2OH^-$$

This electrochemical reaction occurs upon application of approximately −0.4 V to the working electrode relative to a saturated calomel electrode. The hydrogen peroxide triggers the chemiluminescent reaction of the acridinium ester label.

(3) a potential waveform is applied to the electrochemical electrodes such that oxygen is produced at the working electrode by oxidative electrolysis of water. A waveform is then applied to the electrochemical electrodes such that oxygen (precursor) created by the electrolysis of water is reduced to form hydrogen peroxide (trigger). The hydrogen peroxide triggers the chemiluminescent reaction of the acridinium ester label.

The chemiluminescence is measured using a Hamamatsu R374 photomultiplier tube centered above the flow cell where particles have concentrated in the collection zone on the working electrode.

EXAMPLE 9

Preparation of Physically Adsorbed Sheep Anti-Thyroid Stimulating Hormone (TSH) Coated Dynal Particles 1 mL of 4.5 µm uncoated magnetic, polystyrene particles with —OH residues on their surface (DYNAL, DYNA- BEADS M-450, DYNAL A.S. Oslo, Norway) is washed by magnetic separation with a 150 mM sodium carbonate/bicarbonate pH 9.6 solution using 2 mL/wash. 0.5 mg of purified monoclonal anti-TSH antibody (Catalog No. 5064031, Ventrex Laboratories, Inc., Portland, Me.) in 1 mL of the carb/bicarb solution is added to the particles. This mixture is incubated overnight at room temperature with mixing. The solution is then magnetically separated from the particles and removed. 1 mL of 3% BSA/PBS with 0.05% sodium azide is added and incubated 2 hours at room temperature with agitation to block unreacted sites. The particles are washed 5 times (2 mL/wash) and then finally resuspended in 1 mL of the same buffer for storage. The final concentration is 3% by weight.

EXAMPLE 10

One Step Separation Sandwich Assay for Thyroid Stimulating Hormone (TSH)

100 µL serum calibrators (London Diagnostics TSH LumiTAG Kit), 25 µL LumaTag TSH acridinium ester-labeled antibody (London Diagnostics) in phosphate buffer and 25 µL anti-TSH-DYNAL particles (Example 9) in phosphate buffer are combined and incubated in polypropylene tubes for 15 minutes, at room temperature, with mixing. The particles are then washed by magnetic separation and then resuspended in 500 µL of pH 4, 10 mM carbonate/bicarbonate buffer. This wash procedure was repeated two additional times. The particles are drawn into a flow cell (Example 3), magnetically collected and the chemiluminescence is excited and measured as described in Example 8. The chemiluminescent intensity is directly proportional to the concentration of analyte present in the sample (increasing intensity as the concentration of analyte increases).

EXAMPLE 11

One Step Non Separation Sandwich Assay for Thyroid Stimulating Hormone (TSH)

100 µL serum calibrators (London Diagnostics TSH LumiTAG Kit), 25 µL LumaTag TSH acridinium ester-labeled antibody (London Diagnostics) in phosphate buffer and 25 µL anti-TSH-DYNAL particles (Example 9) in phosphate buffer are combined and incubated in polypropylene tubes for 15 minutes, at room temperature, with mixing. Prior to reading results, 1 mL of pH 4 100 mM carbonate/bicarbonate buffer is added. The particles are drawn into a flow cell (Example 3), magnetically collected and the chemiluminescence is excited and measured as described in Example 8. The chemiluminescent intensity is directly proportional to the concentration of analyte present in the sample (increasing intensity as the concentration of analyte increases).

What is claimed is:

1. An apparatus for performing a chemiluminescent binding assay utilizing a chemiluminescent label to determine whether or in what amount an analyte of interest is present in a sample comprising:
   (a) a cell defining a sample volume having a vertically elongated columnar zone and having separate inlet and outlet means, and further including means for generating a magnetic field, and having an electrode positioned below a substantial volume of said cell and said vertically elongated columnar zone for triggering the oxidation or reduction of said chemiluminescent label;
   (b) means for impressing a voltage upon said electrode effective to trigger said oxidation or reduction of the chemiluminescent label; and
   (c) means for measuring an indication of whether said analyte is present, or the amount of said analyte present, wherein said indication correlates to the amount of chemiluminescence generated at the collection zone.

2. An apparatus as defined in claim 1, wherein said measurement means comprises a photomultiplier tube.

3. An apparatus as defined in claim 1, wherein said measurement means directly measures chemiluminescence emitted at the collection zone.

4. An apparatus as defined in claim 1, further comprising means for reflecting chemiluminescence generated at the collection zone onto said measurement means.

5. An apparatus as defined in claim 1, wherein said cell further comprises a counter electrode.

6. An apparatus as defined in claim 1, wherein said cell further comprises a reference electrode.

7. An apparatus as defined in claim 1, further comprising a housing enclosing said cell and shielding said measurement means from external light during chemiluminescence.

8. An apparatus as defined in claim 1, further comprising a shutter mechanism provided between said cell and said measurement means.

9. An apparatus as defined in claim 8, wherein said shutter mechanism is controllably operated to open only so far as to expose the measurement means to the collection zone in the cell during chemiluminescence.

10. An apparatus as defined in claim 1, further comprising a pump suitable for providing fluid transport to, through and from said cell.

11. An apparatus as defined in claim 10, wherein said pump is a peristaltic pump.

12. An apparatus as defined in claim 10, wherein said pump is a positive displacement pump.

13. An apparatus for performing a chemiluminescent binding assay utilizing a chemiluminescent label to determine whether or in what amount an analyte of interest is present in a sample comprising:
   (a) a cell defining a sample volume having a vertically elongated columnar zone and having separate inlet and outlet means, said sample volume further having a collection zone on a surface of an electrode positioned below a substantial volume of said cell and said vertically elongated columnar zone, said electrode being for triggering the oxidation or reduction of said chemiluminescent label;
   (b) means for generating a magnetic field at said collection zone, wherein said means for generating said magnetic field is positioned proximate to said cell;
   (c) means for impressing a voltage upon said electrode effective to trigger said oxidation or reduction of the chemiluminescent label; and
   (d) means for measuring an indication of whether said analyte is present, or the amount of said analyte present, wherein said indication correlates to the amount of chemiluminescence generated at the collection zone.

14. An apparatus as defined in claim 13, wherein said measurement means does so by directly measuring chemiluminescence emitted at the collection zone.

15. An apparatus as defined in claim 13, further comprising means for reflecting chemiluminescence generated at the collection zone onto said measurement means.

16. An apparatus as defined in claim 13, further comprising a shutter mechanism provided between said cell and said measurement means.

17. An apparatus as defined in claim 16, wherein said shutter mechanism is controllably operated to open only so far as to expose the measurement means to the collection zone in the cell during chemiluminescence.

18. An apparatus as defined in claim 13, further comprising a pump suitable for providing fluid transport to, through and from said cell.

19. An apparatus as defined in claim 18, wherein said pump is a peristaltic pump.

20. An apparatus as defined in claim 18, wherein said pump is a positive displacement pump.

* * * * *